(12) United States Patent
Mott et al.

(10) Patent No.: US 6,399,290 B1
(45) Date of Patent: Jun. 4, 2002

(54) SILVER HALIDE IMAGING MATERIALS

(75) Inventors: Andrew W. Mott, Bishops Stortford; Kevin P. Hall, Leaden Roding, both of (GB)

(73) Assignee: Eastman Kodak Company, Rochester, NY (US)

(*) Notice: Subject to any disclaimer, the term of this patent is extended or adjusted under 35 U.S.C. 154(b) by 0 days.

(21) Appl. No.: 09/396,187

(22) Filed: Sep. 14, 1999

Related U.S. Application Data

(62) Division of application No. 08/002,150, filed on Jan. 11, 1993, now abandoned.

(30) Foreign Application Priority Data

Jan. 13, 1992 (GB) .............................................. 9200632

(51) Int. Cl.[7] .............................. G03C 1/815; G03C 1/83
(52) U.S. Cl. ........................ 430/507; 430/512; 430/522
(58) Field of Search ............................... 430/512, 522, 430/594, 507

(56) References Cited

U.S. PATENT DOCUMENTS

| | | | | |
|---|---|---|---|---|
| 3,379,533 A | * | 4/1968 | Jenkins et al. | |
| 3,389,994 A | * | 6/1968 | Pillet et al. | |
| 3,984,247 A | * | 10/1976 | Nakamura et al. | 430/522 |
| 4,925,782 A | * | 5/1990 | Okada | 430/512 |

FOREIGN PATENT DOCUMENTS

EP 460550 * 12/1991

OTHER PUBLICATIONS

Metwally Et Al, Chem Abs. vol. 100, 1984, No. 103, 122d.*

* cited by examiner

Primary Examiner—Richard L. Schilling
(74) Attorney, Agent, or Firm—J. Lanny Tucker

(57) ABSTRACT

Compounds suitable for use as acutance, antihalation and filter dyes in silver halide imaging materials having a nucleus represented by a compound comprising a nucleus represented by one of the following general formulae (I) and (II):

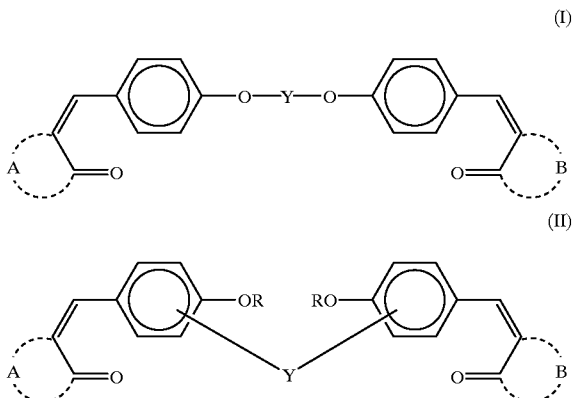

in which;

A and B independently represent those non-metallic atoms necessary to complete a neutral heterocyclic ring in which at least one ring atom is nitrogen, R represents hydrogen or an alkyl group, and Y represents a divalent aliphatic linking group.

10 Claims, No Drawings

SILVER HALIDE IMAGING MATERIALS

CROSS-REFERENCE TO RELATED APPLICATION

This is a Divisional of application Ser. No. 08/002,150 filed Jan. 11, 1993 now abandoned.

FIELD OF THE INVENTION

This invention relates to silver halide imaging materials and is particular to a class of compounds which are suitable for use as acutance, antihalation and filter dyes for such materials. The invention also relates to a method of preparing the aforesaid compounds.

BACKGROUND TO THE INVENTION

It is a common practice with silver halide imaging materials to colour the light sensitive photographic emulsion and/or other hydrophilic colloid layers so as to absorb light of a specified wavelength or wavelengths. For example, where it is necessary or desirable to control the spectral energy distribution of light entering the emulsion layer, a coloured layer known as a "filter layer" can be interposed between the emulsion layer and the exposure source. Where the photographic material comprises a plurality of such photographic emulsion layers, the filter layer may be interposed between successive emulsion layers.

A coloured layer may also be interposed between the photographic emulsion and the support to prevent halation. Halation, which is the spreading or blurring of the photographic image in regions of intense exposure due to the formation of a halo around the image, is caused by light reflected from an interface between two layers, such as the emulsion layer and support, the light being scattered back into the emulsion layer. The coloured layer may also be present on the reverse, uncoated side of the support to prevent the reflection of light from the surface thereof. These coloured layers are collectively referred to as "antihalation layers". Where the photographic material comprises a plurality of emulsion layers, an antihalation layer may be interposed between every adjacent plurality of layers.

The photographic emulsion layer itself may be coloured to present any reduction in image sharpness caused by light scattering in the emulsion layer. The dyes used to colour the emulsion layer are known as "acutance dyes".

The photosensitive emulsion and other hydrophilic colloid layers are normally coloured by the addition of a dye to the coating formulation. Such a dye desirably exhibits the following characteristics.

(1) It should have adequate spectral absorption in compliance with the intended use.
(2) It should be photochemically inert. In other words, it should not produce chemically adverse effects (e.g., decrease of sensitivity, fading of latent image and fogging) on the performance of the silver halide photographic emulsion layer.
(3) It should decolourise or dissolve in the processing solution (or water) during photographic processing and should not leave undesirable colours in the photographic light-sensitive material after being processed.
(4) It should not diffuse from the coloured layer to the other layers.
(5) It should be stable and resistant to discolouration in solution and the photographic material for extended periods of time.

It is particularly important that the dye should not diffuse from the coloured layer to adjacent layers. Otherwise, not only are those other layers subject to an adverse spectral effect, but the performance of the coloured layer itself may be markedly affected.

A number of dyes said to be suitable for use in photographic materials are known in the art, including: oxonol dyes, such as those disclosed in British Patent No. 506385 and 1278621 and U.S. Pat. Nos. 3,247,127, 2,533,472 and 3379533; hemioxonol dyes, such as those disclosed in British Patent No. 584509; styryl dyes, such as those disclosed in U.S. Pat. No. 2298733; merocyanine dyes, such as those disclosed in U.S. Pat. No. 2,493,747; cyanine dyes, such as those disclosed in U.S. Pat. No. 2,843,486, and pyrazolone dyes, such as those disclosed in U.S. Pat. Nos. 3,002,837, 3,389,994 and 4,925,782. The dyes are decolourised during processing of the exposed photographic material, typically by reaction with sulphite (or acid sulphite) contained in the developer solution and/or alkaline conditions in combination therewith, as disclosed, for example, in British Patent No. 506385.

However, as many known dyes do not generally exhibit all of the above five characteristics, there is a continuing need for dye compounds that can satisfy the aforesaid criteria.

A class of compounds has now been found which are particularly suitable for use as acutance, antihalation and filter dyes in silver halide imaging materials.

BRIEF SUMMARY OF THE INVENTION

According to one aspect of the present invention there is provided a compound comprising a nucleus represented by one of the following general formulae (I) and (II):

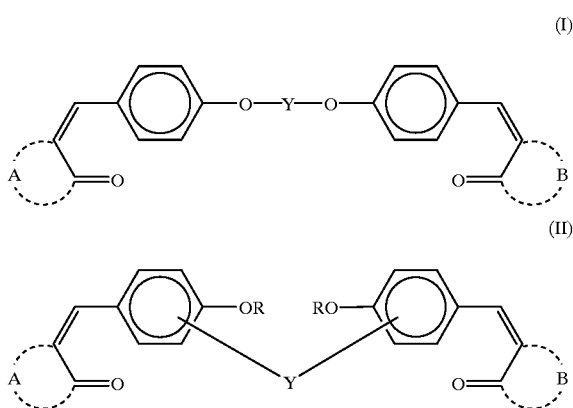

in which;

A and B independently represent those non-metallic atoms necessary to complete a neutral (i.e., non-charged) heterocyclic ring in which at least one ring atom is nitrogen, R represents hydrogen or an alkyl group, and Y represents a divalent aliphatic linking group.

The class of compounds represented by general formulae (I) and (II) absorb light in the UV/VIS (blue) region of the spectrum, particularly at wavelengths between 360 and 450 mm (inclusive). They may be incorporated into conventional silver halide photographic materials to selectively colour one or more layers of the material for acutance, antihalation and filter purposes, but without adversely affecting the photographic characteristics, especially the spectral sensitisation, of the photographic emulsion. The compounds of formulae (I) and (II) are substantive, having a reduced tendency to diffuse into adjacent layers, and are decolourisable by conventional photographic processing. The compounds of formulae (I) and (II) also show good stability and are resistant to bleaching on storage.

Therefore, according to a further aspect of the present invention there is provided a light-sensitive silver halide photographic material comprising a support having coated thereon in one or more layers a photographic silver halide emulsion, which photographic material comprises in either the silver halide emulsion layer(s) and/or an auxiliary layer as an acutance, antihalation or filter dye, a compound of formula (I) or (II).

DESCRIPTION OF PREFERRED EMBODIMENTS

The groups completed by A and B are generally 5, 6 or 7-membered heterocyclic rings, the constituent atoms of which are normally selected from C,N,O,S and Se, but with the proviso that at least one ring atom is nitrogen. The heterocyclic rings may optionally possess one or more substituents selected from alkyl groups (e.g., methyl, ethyl, isopropyl etc.), halogen atoms (e.g., fluorine, chlorine, bromine and iodine), a hydroxy group, alkoxy groups (e.g., methoxy, ethoxy etc.), aryloxy groups (e.g., phenoxy, hydroxyphenoxy etc.), amino groups (e.g., amino, methylamino, dimethylamino etc.), a cyano group, acylamino groups (e.g., acetylamino, benzoylamino etc.), diacylamino groups (e.g., succinimido etc.), ureido groups (e.g., methylureido etc.) sulphonamido groups (e.g., methanesulphonamide etc.), acyloxy groups (e.g., acetyloxy etc.), sulphamoyl groups (e.g., N-ethylsulphamoyl etc.), alkylcarbonyl groups,. arylcarbonyl groups, alkoxycarbonyl groups (e.g., methoxycarbonyl, is ethoxycarbonyl etc.), aryloxycarbonyl groups (e.g., phenoxycarbonyl etc.), alkoxycarbonyl amino groups (e.g., ethoxycarbonylamino etc.), carbamoyl groups (e.g., N-ethylcarbamoyl etc.), aryl groups (e.g., phenyl, tolyl etc.), hydroxyalkyl groups (e.g. hydroxyethyl, hydroxypropyl etc.), alkoxyalkyl groups (e.g., methoxyethyl, methoxypropyl etc.), mercapto groups, alkylthio groups, arylthio groups, alkylsulphonyl groups, arylsulphonyl groups, acyl groups, aralkyl groups, alkyl groups containing a carboxyl group (e.g., carboxymethyl, carboxyethyl etc.), each of which groups may, where appropriate comprise up to 14, preferably up to 10 carbon atoms, and those non-metallic atoms necessary to complete a fused ring substituent incorporating at least two ring atoms of the heterocyclic ring and generally comprising up to 14 ring atoms in toto.

As is well understood in this technical area, a large degree of substitution is not only tolerated, but is often advisable. As a means of simplifying the discussion and recitation of these groups, the terms "group" and "moiety" are used to differentiate between chemical species that allow for substitution or which may be substituted and those which do not or may not be so substituted. For example, the phrase "alkyl group" is intended to include not only pure hydrocarbon alkyl chains, such as methyl, ethyl, octyl, cyclo-hexyl, iso-octyl, tertbutyl and the like, but also alkyl chains bearing conventional substituents known in the art, such as hydroxyl, alkoxy, phenyl, halogen atoms (F, Cl, Br and I), cyano, nitro, amino etc. The phrase "alkyl moiety" on the other hand is limited to the inclusion of only pure hydrocarbon alkyl chains, such as methyl, ethyl, propyl, cyclohexyl, iso-octyl, t-butyl and the like.

Generally, A and B complete identical groups and examples of preferred muclei include: isoxazolone, pyridone,barbituric acid, thiobarbituric acid, 2-pyrazolin-5-one, oxazolidinedione, 2-thio-oxazolidinedione, oxindole, rhodanine, hydantoin, 2-thiohydantoin etc.

In order to incorporate the compounds of general formulae (I) or (II) into the largely hydrophilic colloid layers of silver halide photographic materials, it may be desirable and indeed essential in some cases to provide one or both of the heterocyclic rings completed by A and B with one or more water-solubilising groups. Such groups are well known in the art and comprise moieties, such as sulphonic acid, sulphonic acid salts (with an associated cation, e.g., alkali earth cations, $\oplus NH(C_2H_5)_3$,

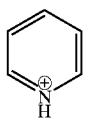

etc.), carboxylic acid, carboxylic acid salts, —OH, phosphoric acid and phosphates. The water-solubilising moieties may be attached directly to the rings completed by A & B, but are preferably present as substituents on alkyl or aryl groups that are attached to the rings. Preferred water-solubilising groups are sulphonic acid groups and alkyl sulphonates, generally comprising up to carbon atoms, and aryl sulphonates, generally comprising up to 10 carbon atoms.

A and B preferably represent those non-metallic atoms necessary to complete a nucleus represented by one of the following heterocyclic ring structures:

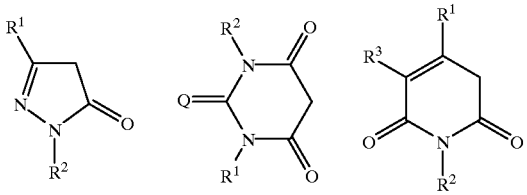

in which;

Q represents O or S, $R^1$ and $R^2$ independently represent hydrogen, an alkyl group comprising up to 10 carbon atoms, an alkoxy group comprising up to 10 carbon atoms, a cycloalkyl group comprising up to 14, preferably up to 10 carbon atoms, or an aryl group comprising up to 14, preferably up to 10 carbon atoms, each of which groups may possess one or more substituents, such as halogen atoms, alkoxy groups comprising up to 5 carbon atoms, aryl groups comprising up to 10 carbon atoms, amide, cyano or a water solubilising group as defined previously; and $R^3$ represents H or any of the substituents defined for A and B previously, but preferably represents an electron-attracting group such as cyano. Examples of groups represented by $R^1$ and $R^2$ include —$CH_3$, —$CH(CH_3)_2$, —$C(CH_3)_3$,

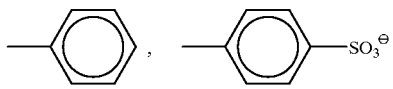

etc. Preferably, at least one of the groups represented by $R^1$ and $R^2$ is a water solubilising group, such as a sulphonated aryl group (e.g., phenyl) comprising up to 10 carbon atoms.

Each phenyl ring of the structures represented by:

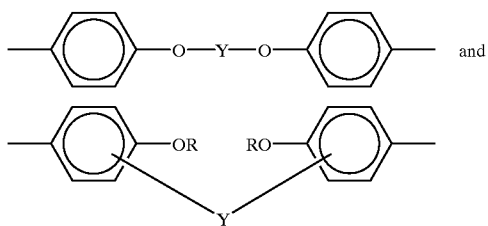

and may optionally possess one or more substituents as defined for A and B previously. Preferred substituents include halogen atoms, hydroxy, alkyl groups, alkoxy groups, amino groups and carbonyl groups, each of which groups may comprise up to 5 carbon atoms, and water-solubilising groups as defined previously.

Preferred compounds of general formulae (I) and (II) have a structure represented by general formula (III) or (IV):

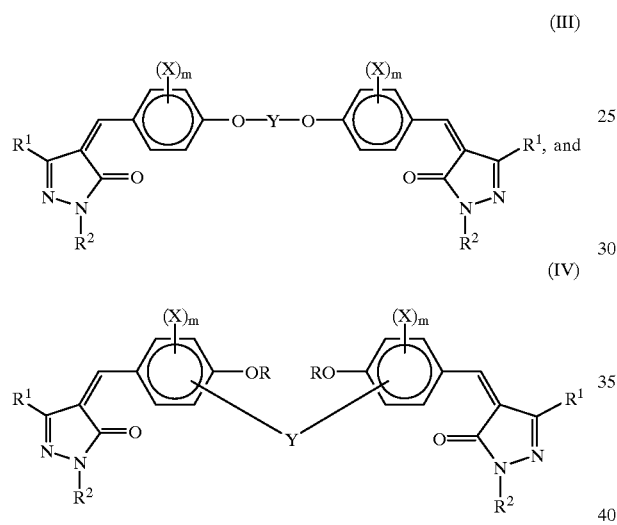

in which;
- each m is independently 0, 1 or 2,
- each X independently represents an alkoxy group, e.g., methoxy, comprising up to 5 and preferably no more than 3 carbon atoms, and
- R, $R^1$, $R^2$ and Y are as defined previously.
- Y may represent any suitable divalent aliphatic linking group known in the art of dye synthesis including groups represented by:

in which;
- n has integral values of from 1 to 10, and

Y preferably represents $(CH_2)_n$ where n has values of 1, 2 or 3.

The linking group may optionally possess one or more substituents, such as halogen atoms, alkyl groups comprising up to 5 carbon atoms, alkoxy groups comprising up to 5 carbon atoms, aryl groups comprising of up to 10 carbon atoms etc.

The linking group may also include a bridging or rigidising group of the type well known in the art. Such groups generally comprise a 5, 6 or 7-membered heterocyclic or carbocyclic ring or a heterocyclic or carbocylic fused ring system comprising up to 14 ring atoms. Each ring or fused ring system incorporates at least one carbon atom of the linking group within its ring structure with the remainder of the ring atoms being selected from C,N,O,S and Se. Examples of bridging groups include: cyclopentane, cyclohexane, cyclopentene, cyclohexene etc.

R generally represents hydrogen or an alkyl group comprising up to 10 carbon atoms, preferably up to 5 carbon atoms, and which may be substituted in a similar manner to groups represented by $R^1$ and $R^2$.

Examples of preferred compounds prepared in accordance with the present invention are shown in TABLE I hereinafter.

The dyes of general formulae (I) and (II) are prepared by condensing a dimeric aldehyde of formula (V) or (VI) with the appropriate heterocycle precursors represented by (VII) and (VIII). Thus:

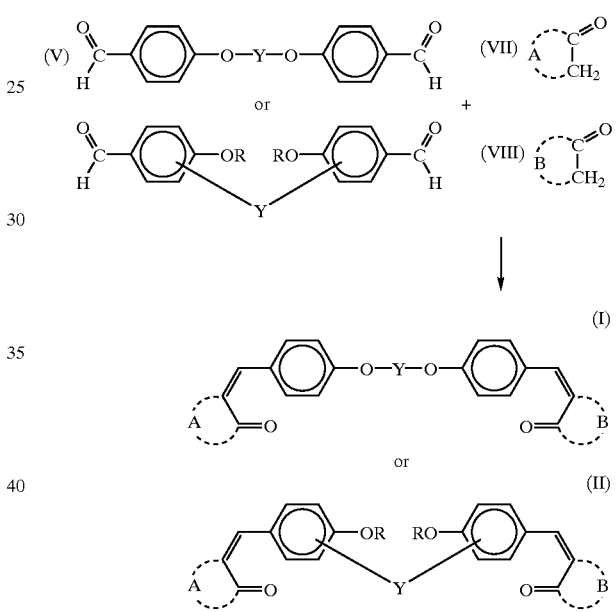

in which;
A, B, R and Y are as defined previously. The aforesaid reaction is advantageously conducted in a solvent which is able to dissolve all of the starting materials. Examples of suitable solvents include: alcohols, acetonitrile, amides and ethers. These solvents may be used individually or in combination with each other to improve the solubility of the starting materials. The reaction is advantageously conducted in the presence of an amine, e.g., triethylamine, to promote the reaction. The reaction is preferably conducted at a temperature of from 50 to 90° C. over a period of about 5 to 24 hours.

The photographic materials of the invention may comprise any suitable silver halide based imaging material including: colour papers, colour negative films, colour reversal films (either with or without couplers), photosensitive materials for printing plates (e.g., lith films), photosensitive materials for use with cathode ray tubes (CRTS) (e.g., x-ray emulsions), photosensitive materials for dye transfer processes (inhibition transfer processes), photosensitive materials for-colour diffusion transfer processes, photosensitive materials for silver salt diffusion transfer processes, photographic emulsion for silver dye-bleach processes, photosensitive materials for thermal development (i.e., photothermographic materials) and photosensitive materials for physical development. Such materials generally comprise a support having coated thereon one or more layers of a photographic silver halide emulsion, typically a gelatino silver emulsion.

The compounds of general formulae (I) and (II) can be incorporated directly into the silver halide emulsion or any auxiliary hydrophilic colloid layer by dissolving or dispersing the compound into the precoating formulation thereof. Alternatively, they may be dissolved in a suitable aqueous solvent, such as an alcohol, e.g., ethanol, propanol etc., a halogenated alcohol/water mixture, pyridine and mixtures thereof, and the resulting solution added to the precoating formulation or the coated layer(s) as a coating final. Where the compounds of formulae (I) and (II) are of a more hydrophobic character, they may be dissolved in a substantially water-insoluble, high boiling point organic solvent (b.p.$\geq$160° C.). Suitable high-boiling point organic solvents include, for example, alkyl esters of phthalic acid, such as dibutyl phthalate and dioctyl phthalate (as disclosed in U.S. Pat. No. 2,322,027); phosphate esters, such as diphenyl phosphate, triphenyl phosphate, tricresyl phosphate and dioctylbutyl phosphate; citrate esters, such as tributyl acetylcitrate; benzoate esters, such as octyl benzoate; alkylamides, such as diethyl laurylamine; fatty acid esters, such as dibutoxyethyl succinate and diethyl acetate, and trimesate esters, such as tributyl trimesate. Other solvents that can be used are organic solvents having a boiling point of from about 30 to about 150° C. They include lower alkyl acetates, such as ethyl acetate and butyl acetate, ethyl propionate, sec-butyl alcohol, methyl isobutyl ketone, 8-ethoxyethyl acetate, methyl cellosolve acetate and other water-soluble solvents, such as methanol and ethanol. The dye and high-boiling point solvent should preferably be used in a ratio of from 1:1 to 1:10 (by weight).

Where the compounds of formulae (I) and (II) are only sparingly soluble in water, they may be introduced into the emulsion/auxiliary layer as a dispersion of finely milled particles.

When used as an acutance, antihalation or filter dye, it is preferred to incorporate the compounds of formulae (I) and (II) in an amount sufficient to provide an optical density of from 0.05 to 3.0 absorbance units. The coating weight of the dye is generally from 0.001 to 1 g/m$^2$, preferably 0.001 to 0.05 g/m$^2$. When used for antihalation purposes the dye must be present in a layer separate from the silver halide emulsion layer(s). The antihalation layer may be positioned either above or below the silver halide emulsion layer(s) and if the support is transparent, the antihalation layer may be positioned on the surface of the support opposite the silver halide emulsion. For acutance purposes, the compounds of formulae (I) and (II) are incorporated within the silver halide emulsion layer(s). When used for filter purposes, the compounds of formulae (I) and (II) are normally incorporated in a layer separate from and positioned above the silver halide emulsion layer(s).

When used for filter purposes in conventional colour negative or reversal films comprising one or more outer layers sensitive to blue light and one or more inner layers sensitised to green and/or red light, the compounds of formula I and II and advantageously incorporated in a layer situated between the blue-sensitive layer(s) and the green- and red-sensitive layers. By this means, ultraviolet and blue light can be prevented from causing unwanted exposure of the green- and red-sensitive layers due to the native sensitivity of the silver halide grains to light of those wavelengths.

The silver halide photographic emulsion may be any of silver bromide, silver iodobromide; silver iodochlorobromide, silver chlorobromide, silver chloride and silver iodochloride. Preferably, the silver halide emulsion is a silver bromide, silver chlorobromide, silver iodobromide or silver iodochlorobromide emulsion. The silver iodide content is preferably not more than 10 mol %, and more desirably is in the range of from 0.1 to 5 mol %.

The silver halide grains in the photographic emulsion may comprise regular crystals of cubic, orthorhombic, tabular, octahedral or tetrahedral habit, or irregular crystals, such as spherical or composite grains.

Each of the silver halide grains may be made up of a uniform phase through its core and surface layer, or it may be dissimilar in phase between the core and the surface. It is also possible to use two or more independently prepared silver halide emulsions as a mixture. In addition, the silver halide particles may be of the surface latent image type or of the internal latent image type. In the former, the latent image is formed on the surface of the grains, and in the latter, the image is formed inside the grains. The surface latent image type of grain is used for negative-type emulsions and the internal latent image type for internal latent image type emulsions and prefogged direct reversal type emulsions.

As regards the average grain size of the silver halide emulsion, fine grains, e.g., 1 $\mu$m (micrometer) or less, are preferred and very fine grains not larger than 0.5 $\mu$m are particularly preferable. While the grain size distribution is optional, a monodispersion is preferable for printing plate and graphic art applications. The term "monodispersion" as used herein means that, whether by in weight or number, at least 95% of grains are sized within ±40% of the mean grain size.

One preferred silver halide emulsion comprises plate grains having a thickness of 0.5 $\mu$m or less, preferably 0.3 $\mu$m or less, and a diameter of 0.6 $\mu$m or greater and in which plate grains having an average aspect ratio of 5 or more, account for more than 50% of their total projected area.

The silver halide emulsions used in this invention can be prepared according to the processes described, for example, in "Chimie et Physique Photographique" by P. Glafkides (Paul Montel, 1967), "Photographic Emulsion Chemistry" by G. F. Duffin (Focal Press, 1966) and "Making and Coating Photographic Emulsion" by V. L. Zelikman (Focal Press 1964).

When the silver halide grains used in this invention are formed, the growth of grains may be controlled by adding a silver halide solvent, such as ammonia, potassium thiocyanate, ammonium thiocyanate and thioether compounds, as disclosed in U.S. Pat. Nos. 3,271,157, 3,574, 628, 3,704,130, 4,297,439 and 4,276,374.

The formation or physical ripening of the silver halide crystals may be carried out in the presence of a cadmium salt, a zinc salt, a lead salt, a thallium salt, an iridium salt or complex salt thereof, a rhodium salt or complex salt thereof or a ruthenuim salt or complex salt thereof, or mixtures thereof.

Gelatin is preferably used as the binder or protective colloid for the silver halide emulsion, but other hydrophilic colloids and extenders can also be employed. For example, other useful materials might include gelatin derivatives, graft copolymers of gelatin to other high polymers, proteins, such as albumin and casein, cellulose derivatives, such as hydroxyethyl cellulose, carboxymethyl cellulose, cellulose sulphate esters, etc., sugar derivatives, such as sodium alginate, starch derivatives etc., and synthetic homo- or copolymers such as polyvinyl alcohol, poly-N-vinyl pyrrolidone, polyacrylic acid, polymethacrylic acid, polyacrylamide, polyvinyl imidazole and polyvinyl pyrazole.

The silver halide emulsion is usually chemically sensitised. The chemical sensitisation may be accomplished by sulphur sensitisation that employs a sulphur-containing compound (e.g., stannous salts, amines, hydrazine derivatives, formamidinesulphinic acid and silane compounds), or noble metal sensitisation that employs a noble metal compound (e.g., a gold complex or complex salts of group VIII metals, such as iridium, platinum, palladium and rhodium). The sensitisation methods may be applied individually or in combination with one another.

Supersensitisers may also be employed.

The photographic emulsions may be high contrast, e.g., lith films, containing a hydrazine compound or other additives known in the art. Such materials are disclosed, for example, in U.S. Pat. Nos. 2,322,027, 2,419,974, 2,419,975, 4,166,742, 4,168,977, 4,211,857, 4,224,401, 4,743,739, 4,272,606, 4,272,614, 4,311,781 and 4,323,643.

The silver halide emulsion may contain a variety of compounds for the prevention of fog that would otherwise occur during the manufacturing process, preservation or photographic processing and for the stabilisation of photographic performance. Examples of such antifoggants and stabilisers include: azoles, such as benzothiazolium salts, nitroimidazoles, nitroindazoles, triazoles, benzotriazoles, benzimidazoles (particularly the nitro- or halogen-substituted benzimidazoles, e.g., bromobenzimidazoles, chlorobenzimidazoles etc.); heterocyclic mercapto compounds, such as mercaptothiazoles, mercaptobenzothiazoles, mercaptobenzimidazoles, mercaptothiadiazoles, mercaptotetrazoles (particularly 1-phenyl-5-mercaptotetrazole), and mercaptopyrimidines; thioketo compounds (e.g., oxazolinethione); azaindenes, such as triazaindenes, tetraazaindenes (particularly 4-hydroxy-substituted-(1,3,3a,7)-tetraazaindenes); benzenethiosulphonic acids; benzenethiosulphinic acids and benzenesulphonamide. Amongst these compounds, benzotriazoles (e.g., 5-methylbenzo-triazole and nitroindazoles (e.g., 5-nitroindazole) are preferred. These compounds may also be incorporated in the processing solution.

The photographic materials may also contain inorganic or organic hardening agents in the photographic emulsion layer or other hydrophilic colloid layer. For this purpose chromium salts (chrome alum, chromium acetate etc.), aldehydes (formaldehyde, glyoxal, glutaraldehyde etc.), N-methylol compounds (dimethylolurea, methyloldimethylhydantoin etc.), dioxane derivatives (2,3-dihydroxydioxane etc.), active vinyl compounds (1,3,5-triacryloyl-hexahydro-s-triazines, 1,3-vinyl-sulphonyl-2-propanol etc.), active halogen compounds (2,4-dichloro-6-hydroxy-s-triazine etc.), mucohalogenic acids (mucochloric acid, mucophenoxychloric acid etc.), and the like may be used. These hardening agents may be incorporated alone or in combination.

The silver halide emulsion or other hydrophilic colloid layer may also contain a variety of surface active agents for purposes, such as the improvement of coating properties, antistatic properties, slip properties, emulsion dispersibility, anti-adhesion properties and photographic properties (e.g., development acceleration, increase in contrast, sensitisation etc.).

Non-ionic surfactants may be employed such as saponin (steroidal) polyethylene glycol, polyethylene glycol/polypropylene glycol condensate, polyethylene glycol alkyl ethers, polyethylene glycol alkyl aryl ethers, polyethylene glycol esters, polyethylene glycol sorbitan esters, polyalkylene glycol alkylamines or alkylamides, silicone polyethylene oxide adducts), glycidol derivatives (e.g., alkenylsuccinic acid polyglyceride, alkylphenol polyglyceride), polyhydric. alcohol-fatty acid esters, sugar alkyl esters etc.

Anionic surfactants containing acid groups, such as a carboxyl group, a sulpho group, a phospho group, a sulphuric acid ester group, a phosphoric acid ester group etc., for example, alkylcarboxylate, alkylsulphonates, alkylbenzenesulphonates, alkylnaphthalenesulphonates, alkylsulphuric acid esters, alkylphosphoric acid esters, n-acyl-n-alkyltaurines, sulphosuccinic acid esters, sulphoalkylpolyoxyethylene alkylphenyl ether, polyoxyethylene alkylphosphoric acid esters etc., may also be used.

Amphoteric surfactants such as amino acids, aminoalkylsulphonic acids, aminoalkylsulphuric or phosphoric acid esters, alkylbetaines, amine oxides etc.; and cationic surfactant, such as alkylamines, aliphatic or aromatic quaternary ammonium salts, heterocyclic quaternary ammonium salts, such as pyridinium salts, imidazolium salts etc., aliphatic or heterocyclic ring-containing phosphonium or sulphonium salts etc. may be used.

The photographic emulsion layer and/or the hydrophilic colloid layer may also include a matting agent, such as silica, magnesium oxide, polymethyl methacrylate etc., for the purpose of preventing adhesion.

The silver halide emulsion may contain a discolouration prevention agent, hardening agent, colour-fog preventing agent, UV light absorber, protective colloid, such as gelatin, and other additives. Detailed description of these additives will be found in Research Disclosure Vol. 176 (1978, XII) RD-17643.

The finished emulsion is applied to a support which may be made of an opaque material, such as baryta paper, resin-coated paper, synthetic paper or a transparent material, such as glass or a plastics film, e.g., cellulose triacetate; cellulose diacetate, nitrocellulose, polystyrene, polyethylene terephthalate (polyester) etc.

The photographic material of the invention can be exposed using conventional sources, such as natural light (sunlight), tungsten lamps, fluorescent lamps, mercury lamps, xenon arc lamps, carbon arc lamps, xenon flash lamps and CRT spots. The exposure time is not limited to that for ordinary cameras ($\frac{1}{1000}$ sec to 1 sec) and exposures as short as $\frac{1}{10^4}$ to $\frac{1}{10^7}$ by a xenon flash lamp or laser scanner are also possible. Exposures longer than 1 second are also possible. If necessary, it is possible to control the spectral energy distribution of the light for exposure by means of a proper colour filter. The light-sensitive material of the invention can be exposed with laser light or light emitted by the fluorescent material excited by electron ray, X-ray, γ-ray, or α-ray.

The light-sensitive material of the invention may be processed by any known method with any known processing solution, such as those disclosed in Research Disclosure No. 176, pp. 28–30 (RD-17643). Thus, for example, dihydroxybenzenes (e.g., hydroquinone), 3-pyrazolidones (e.g., 1-phenyl-3-pyrazolidone and 4,4-dimethyl-1-phenyl-3-pyrazolidone), aminophenols (e.g., 4-methylaminophenol) etc., can be used alone or in combination.

This invention will now be described with reference to the following Examples.

EXAMPLE 1

Compound A was synthesised according to the following protocol:

4,4'-diformyl-1,2-diphenoxyethane (1 g) and 3-methyl-1,4-sulphophenyl-5-pyrazolone (1.9 g) were refluxed in ethanol (100 ml) containing triethyl amine (0.79 g) for 14 hours. On cooling a solid precipitate was collected by filtration and washed with ethanol. Yield=1.8 g of a yellow solid ($\lambda$max 375 nm).

Compounds B to M were prepared using a similar procedure but starting from the appropriate precursors.

Compounds N and O were prepared by reaction of the appropriate dialdehydes with the sodium salt of 1-ethyl-3-cyano-4-sulphomethylpyridine-2,6-dione (prepared as described in British Patent No. 1448096). The reactions were carried out in refluxing ethanol.

TABLE I

| COMPOUND | | $\lambda$max (nm) $H_2O$ solution |
|---|---|---|
| A | 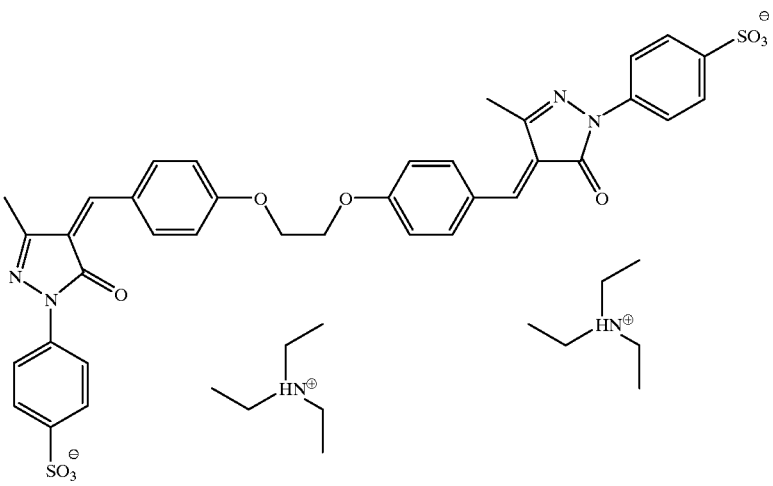 | 375 |
| B | 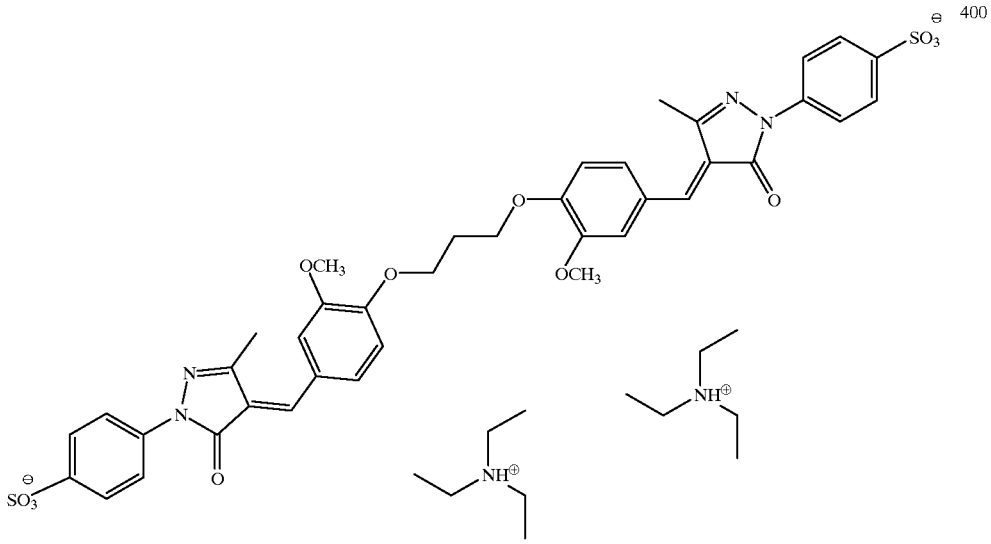 | 400 |

TABLE I-continued
| COMPOUND | | λmax (nm) H₂O solution |
|---|---|---|
| C | 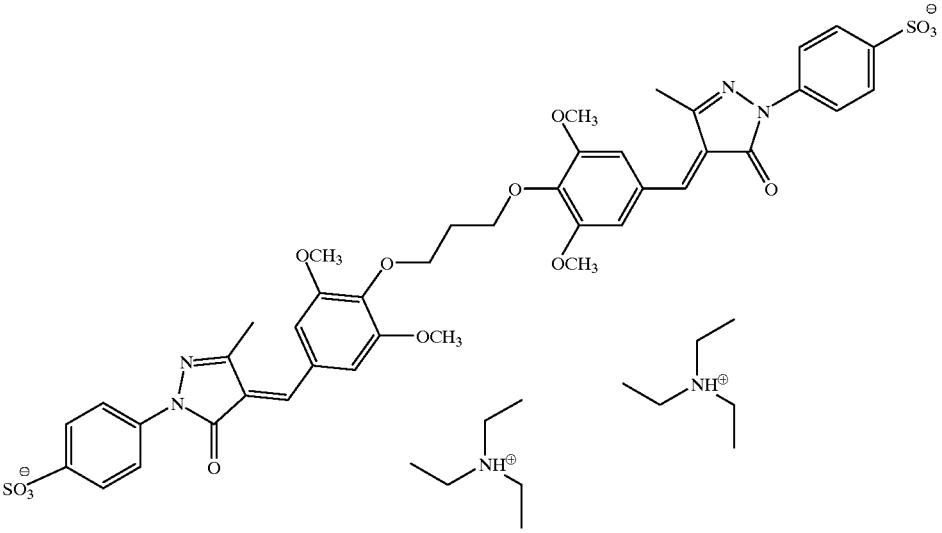 | 415 |
| D | 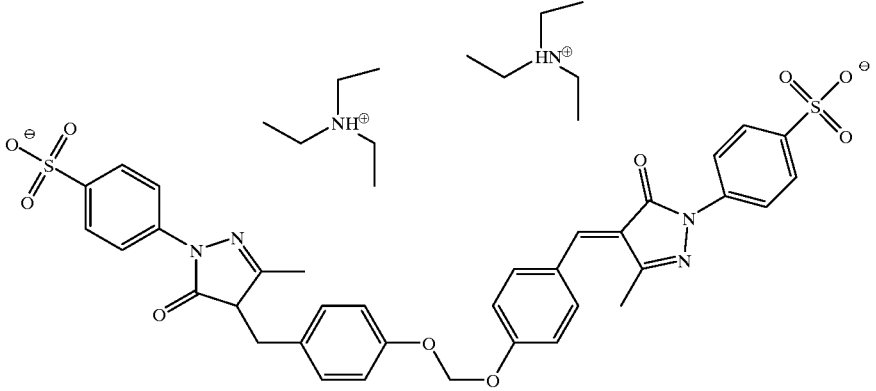 | 370 |
| E | 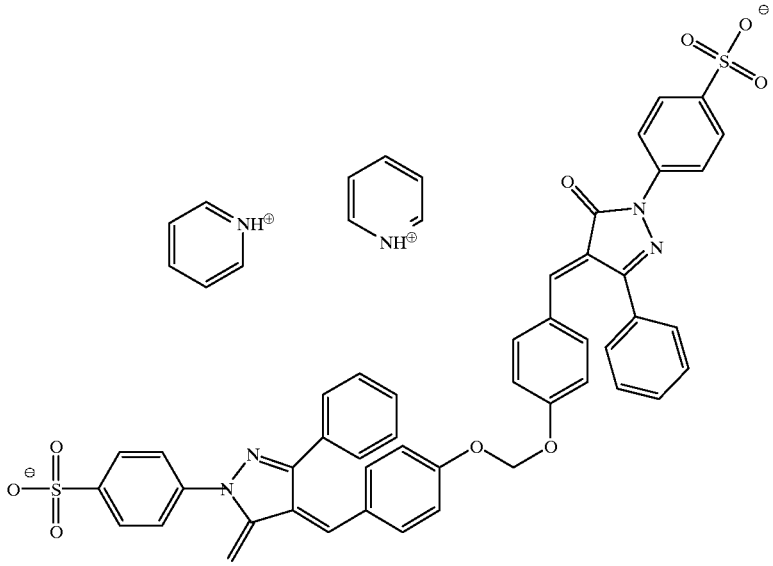 | 390 |

TABLE I-continued

| COMPOUND | | λmax (nm) H₂O solution |
|---|---|---|
| F | (structure) | 380 |
| G | (structure) | 380 |
| H | (structure) | 380 |

TABLE I-continued
| COMPOUND | λmax (nm) H₂O solution |
|---|---|
| I 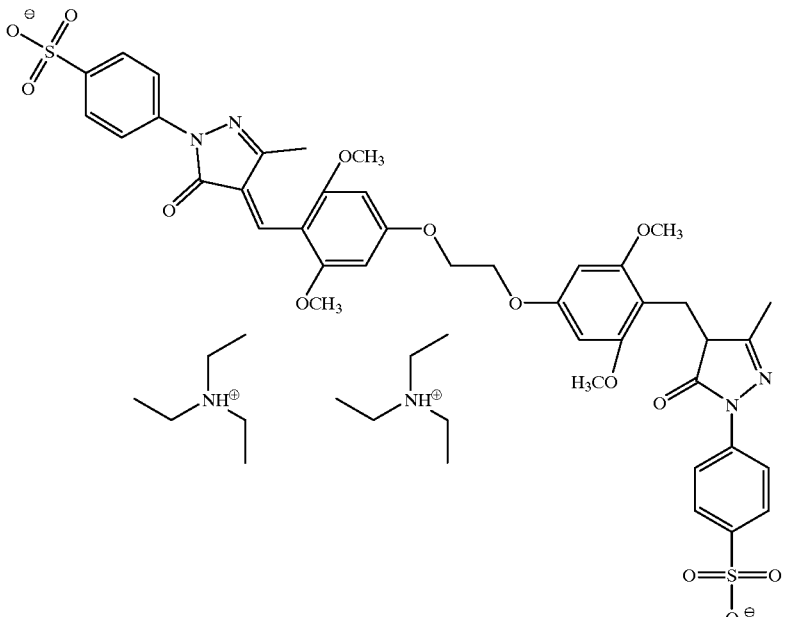 | 387 |
| J 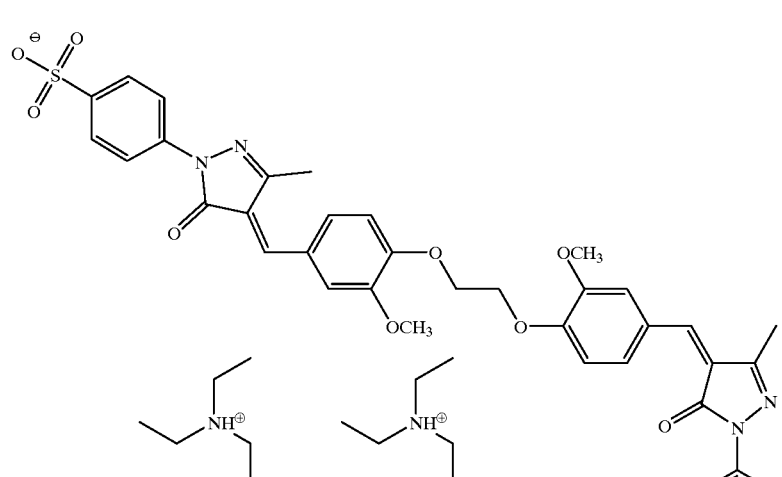 | 409 |

TABLE I-continued
| COMPOUND | | λmax (nm) H₂O solution |
|---|---|---|
| K | 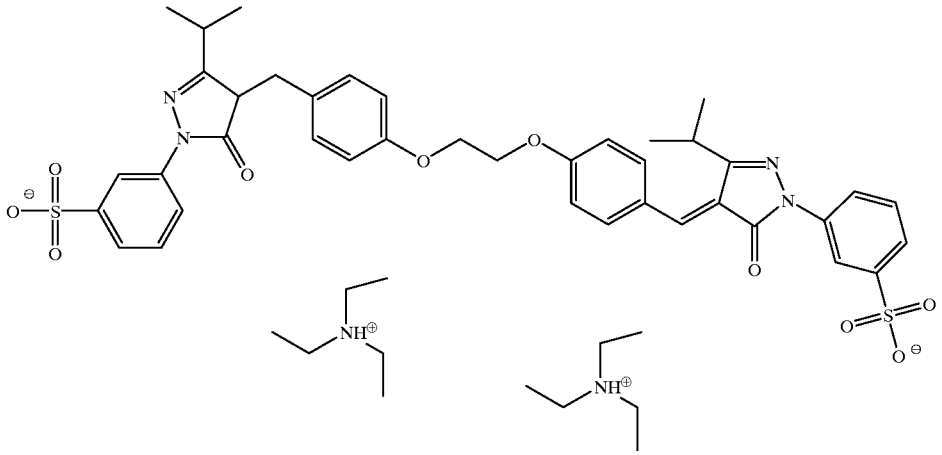 | 362 |
| L | 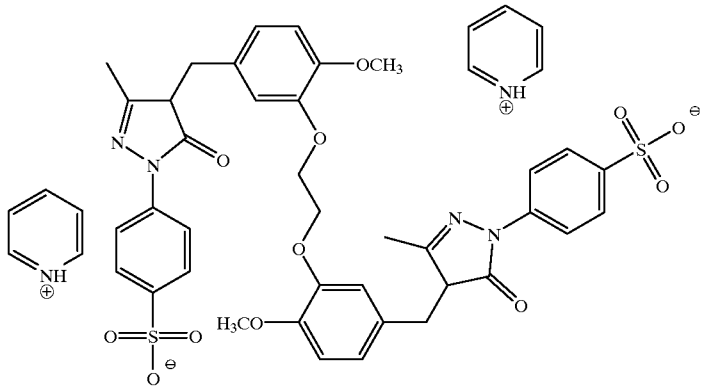 | 380 |
| M | 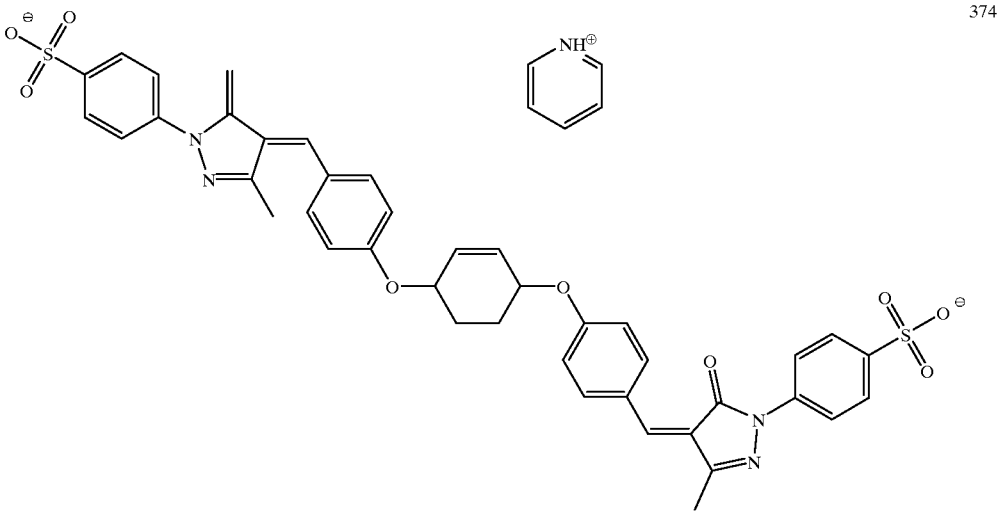 | 374 |

TABLE I-continued

| COMPOUND | | λmax (nm) H₂O solution |
|---|---|---|
| N | 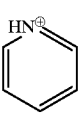 | 440 (in Methanol) |
| O | 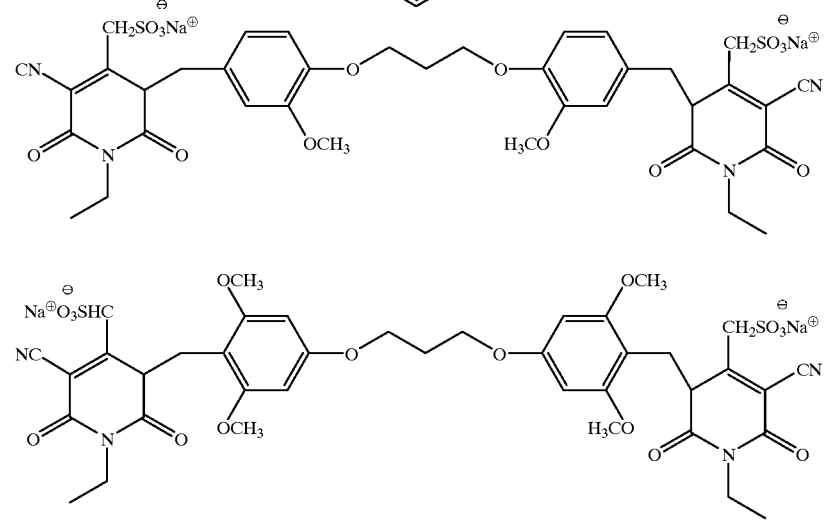 | 455 |

EXAMPLE 2

This Example demonstrates the use of Compound A as an antihalation dye for conventional silver halide photographic materials.

An aqueous gelatin solution was prepared according to the following formation:

| | |
|---|---|
| Compound A | 1.136 g |
| gelatin | 15.6 g |
| deionised water | 120 ml |
| TRITON X-200 (a surfactant commercially available from Rohm & Haas; 4% solution) | 4 ml |
| formaldehyde (4% solution) | 4 ml |

The gelatin solution was coated onto samples of a conventional clear polyester support to give an optical density of 0.48 at 361 nm (λmax). A silver chlorobromide emulsion (96 Cl:4Br, 0.1 μm grain size) with a conventional gelatin top coat was then coated onto the support either (a) on top of the gelatin antihalation layer (Element I) or (b) onto the rear side of the support opposite that bearing the antihalation layer (Element II). The silver chlorobromide emulsion layer and gelatin top coat were also coated onto samples of the support bearing no antihalation layer as a control (Control Element). Once dry, each Element was then exposed through a 0 to 2.6 graduated filter to a SPEKTRAPROOF U.V. source (4 units of full power exposure). The exposed elements were processed using conventional 3M RDCII Chemistry (35 seconds at 30° C.) and 3M FIX ROLL fixer, both of which are commercially available from Minnesota Mining and Manufacturing Co. The sensitometry obtained is given in TABLE II below.

TABLE II

| Element | Dmin | Speed (log) | −1 | −2 | −3 | Dmax |
|---|---|---|---|---|---|---|
| I | 0.05 | 1.06 | 2.4 | 4.2 | 10.1 | 4.3 |
| II | 0.04 | 1.13 | 1.8 | 4.9 | 12.2 | 4.3 |

The films were then tested for their dry etching characteristics by contacting the films with a test dot screen and subjecting them to a variety of exposures to determine how easily dot exposures could be altered by overexposure while maintaining the integrity of the shadow (e.g., 90%) dots. It was found that superior dry etching characteristics were obtained using the dye underlayer construction of Element I when compared with dye backing layer construction of Element II.

EXAMPLE 3

In order to test the mobility and bleaching characteristics of the compounds of the invention, a small amount of each of Compounds A to D and F to L was dissolved in an appropriate solvent e.g., water, methanol, ethanol or a combination thereof. The resulting solution (Solution I) was then added to a gelatin preparation (Solution II) containing a high level of a cross-linking agent and surfactant and the mixture warmed to 45° C. before coating onto clear subbed polyester using a wire wound bar. The coatings were allowed to dry and left for 24 hours at room temperature to harden. Typically the following procedure was used:

Solution I:

Compound=50 mg

Solvent=10 ml

Solution II: 20 g of the following:

gelatin=16 g;

HOSTAPUR SAS=2 ml; (a surfactant commercially available from Hoechst 1% solution formaldehyde=10 ml, and (10% solution)

water=190 g

Individual samples of each coating were then. processed as follows:

I Processed through an Agfa COPY PROOF WD37 washer/drier at room temperature to test mobility of dye at 20° C.

II Processed by agitating in a large volume of water at 45° C. for 30 seconds.

III Processed through a photographic rapid access processor containing 3M RDCV developer and 3M FIX ROLL fixer (70 cm and 35° C. per bath) respectively.

Transmission absorption spectra were then run to obtain peak positions and absorption values compared to the unprocessed material. The results are shown in TABLE III below.

TABLE III

| Element | Compound | Absorbance I | II | III | Maximum Wavelength* (nm) |
|---|---|---|---|---|---|
| III | A | 97 | 40 | <2 | 360 |
| IV | B | 66 | <3 | <2 | 390 |
| V | C | 96 | 60 | <2 | 380 |
| VI | D | 90 | 57 | <2 | 367 |
| VII | F | 95 | 75 | <2 | 365 |
| VIII | G | 97 | 94 | <2 | 360 |
| IX | H | 97 | 92 | <2 | 360 |
| X | I | 97 | 78 | <2 | 387 |
| XI | J | 97 | 91 | <2 | 409 |
| XII | K | 96 | 87 | 30 | 362 |
| XIII | L | 95 | 68 | <2 | 380 |

*as recorded for the gelatin coating. Some values are shifted from the values recorded for aqueous solutions in TABLE I.

Processing conditions I and II test the substantivity of the dyes, i.e., their resistance to leaching from the layer in which they are coated, conditions II being the more severe test. The results show that all the dyes are substantive at 20°, and most are substantive at 45°, thereby indicating that the dyes would not migrate to adjacent layers during the coating of multilayer photographic elements.

Processing conditions III test the ability of the dyes to bleach on treatment with conventional photographic developer. This is important because the final photographic image should not be contaminated by dye stain. All the dyes tested show good bleaching characteristics.

EXAMPLE 4

The mobility and bleachability of Compound M of TABLE I was tested in the following way. An aqueous gelatin solution of Compound M was prepared as follows at 40° C.:

| | |
|---|---|
| gelatin | 1.0 g |
| water | 19 g |
| HOSTAPUR SAS | 2.0 ml |

-continued

| | |
|---|---|
| (1% solution) | |
| Compound M | 0.1 g |
| formaldehyde | 2.0 ml |
| (10% solution) | |

The gelatin solution was coated onto a clear polyester base (175 μm) using a wire wound bar. The coatings were allowed to harden at room temperature for at least 24 hours. The hardened gelatin coating showed a maximum absorbance at 364 nm, and testing gave the following results:

| Test conditions | Absorbance at 364 nm |
|---|---|
| Reference | 100% |
| A | 97% |
| B | 1% |
| C | <1% |

A: 30 seconds at 30° C. in a large volume of water,
B: 30 seconds at 30° C. in Agfa G386b fixer,
C: processed through a Rapid Access processor containing 3M RDCV developer and 3M FIX ROLL fixer (70 cm and 35° C. per bath).

"TRITON X-200" (Rohm & Haas), "3M RDCII", "3M FIX ROLL" and "3M RDCV" (Minnesota Mining & Manufacturing Co.), "SPEKTRAPROOF" and "HOSTAPUR SAS" (Heochst) are all trade names/designations.

What is claimed is:

1. A light-sensitive silver halide photographic material comprising a support having coated thereon in one or more layers a photographic silver halide emulsion, said photographic material comprising in either the silver halide emulsion layer(s) and/or an auxiliary layer, as an acutance, antihalation or filter dye, a compound comprising a nucleus represented by one of the following general formulae (I) and (II):

(I)

(II)

in which;

A and B independently represent those non-metallic atoms necessary to complete a neutral heterocyclic ring in which at least one ring atom is nitrogen, R represents a hydrogen or an alkyl group, and Y represents a divalent aliphatic linking group.

2. The photographic material of claim 1 comprising one or more outer layers sensitive to blue light and one or more inner layers sensitive to green and/or red light and a layer containing said compound of general formulae (I) and (II) positioned between said inner and outer layers.

3. A photographic material of claim 1 6 in which A and B independently represent those non-metallic atoms necessary to complete a 5, 6 or 7-membered heterocyclic ring which may possess one or more substituents selected from alkyl groups, halogen atoms, a hydroxy group, alkoxy groups, aryloxy groups, amino groups, ureido groups, sulphonamide groups, acyloxy groups, sulphamoyl groups, alkylcarbonyl groups, aryloxycarbonyl groups, alkoxycarbonyl amino groups, carbamoyl groups, aryl groups, hydroxyalkyl groups, alkoxyalkyl groups, a mercapto group, alkylthio groups, alkylsulphonyl groups, arylsulphonyl groups, acyl groups, aralkyl groups, alkyl groups containing a carbonyl group and those non-metallic atoms necessary to complete a fused ring substituent incorporating at least two ring atoms of the heterocyclic ring and comprising up to 14 ring atoms in toto.

4. The photographic material of claim 1 in which the heterocyclic ring completed by A or B possesses one or more water-solubilising groups selected from sulphonic acid, sulphonic acid salts, carboxylic acid, carboxylic acid salts, —OH, phosphoric acid and phosphates.

5. The photographic material of claim 1 in which A and/or B represents those non-metallic atoms necessary to complete a heterocyclic ring selected from isoxazolone, barbituric acid, thiobarbituric acid, 2-pyrazolin-5-one, oxazolidinedione, 2-thio-oxazolidinedione, oxindole, rhodanine, hydantoin and 2-thiohydantoin.

6. The photographic material of claim 1 in which A and B independently represent those non-metallic atoms necessary to complete a nucleus represented by one of the following heterocyclic ring structures:

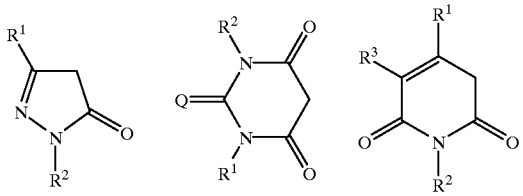

in which;

Q represents O or S, and $R^1$ and $R^2$ independently represent hydrogen, all alkyl group comprising up to 10 carbon atoms, an alkoxy group comprising up to 10 carbon atoms, a cycloalkyl group comprising up to 14 carbon atoms or an aryl group comprising up to 14 carbon atoms, each of which groups may possess one or more substituents selected from halogen atoms, alkoxy groups comprising up to 5 carbon atoms, aryl groups comprising up to 10 carbon atoms, amide, cyano or a water-solubilising group that is sulfonic acid, a sulfonic acid salt, an alkyl sulfonate, an aryl sulfonate, carboxylic acid, a carboxylic acid salt, hydroxy, phosphoric acid, or a phosphate, and $R^3$ represents H or any of the substituents defined for A and B previously.

7. The photographic material of claim 6 wherein said compound nucleus represented by one of general formula (III) and (IV):

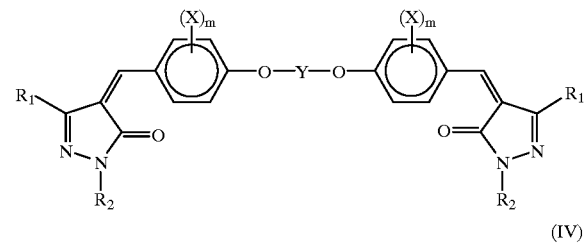

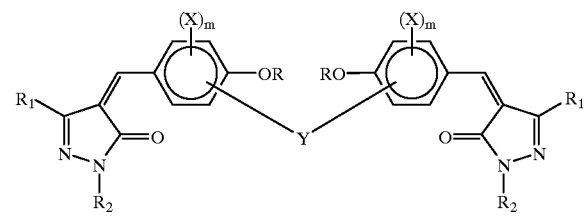

in which;

m is 0, 1 or 2, and each X independently represents an alkoxy group comprising up to 5 carbon atoms.

8. The photographic material of claim 7 in which at least one of those groups represented by $R^1$ and $R^2$ is a water-solubilising group.

9. The photographic material of claim 1 in which Y represents $(-CH_2-)_n$ where n has integral values of from 1 to 10, or

10. The photographic material of claim 1 wherein said compound comprises a nucleus represented by one of the following structures:

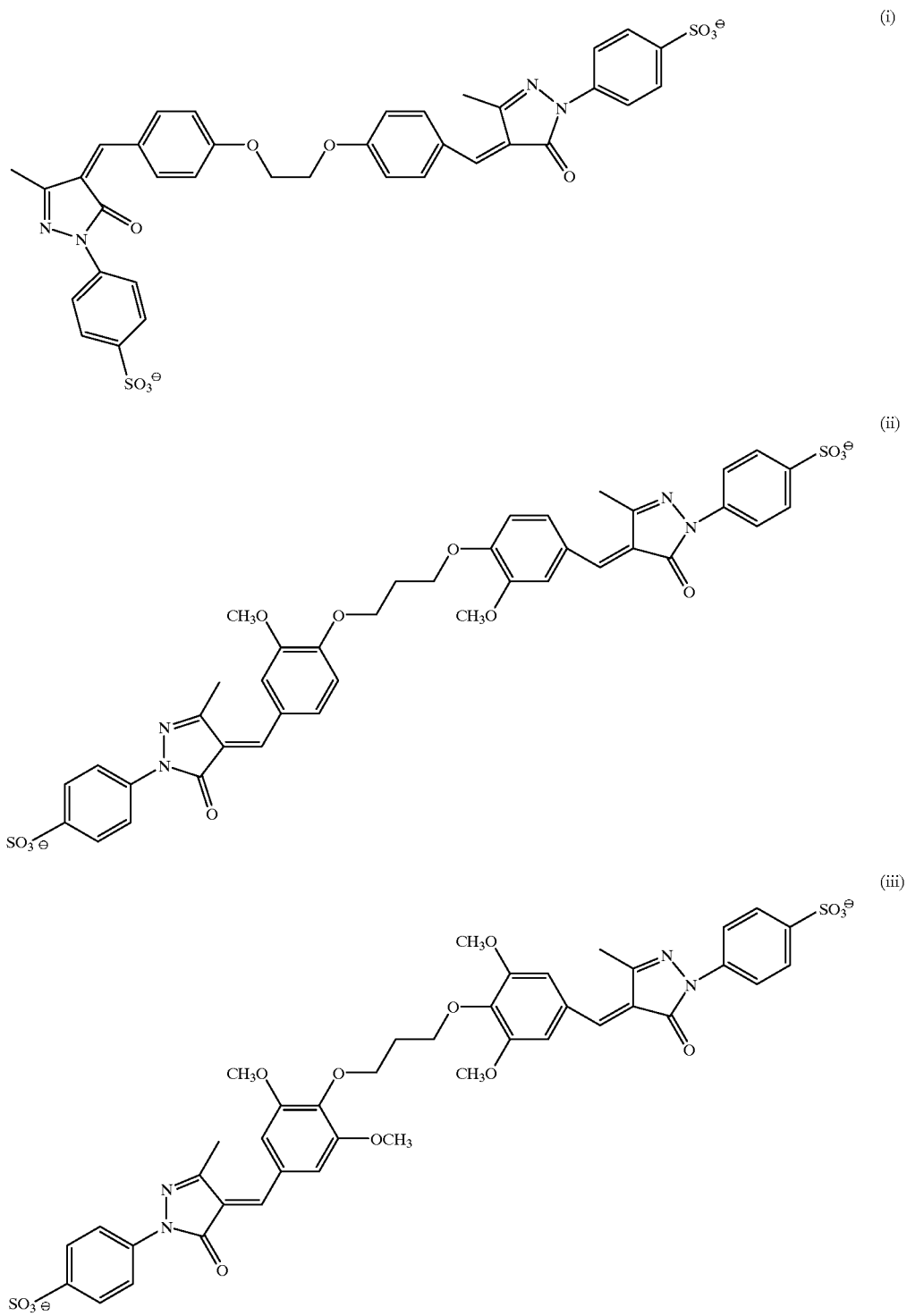

-continued
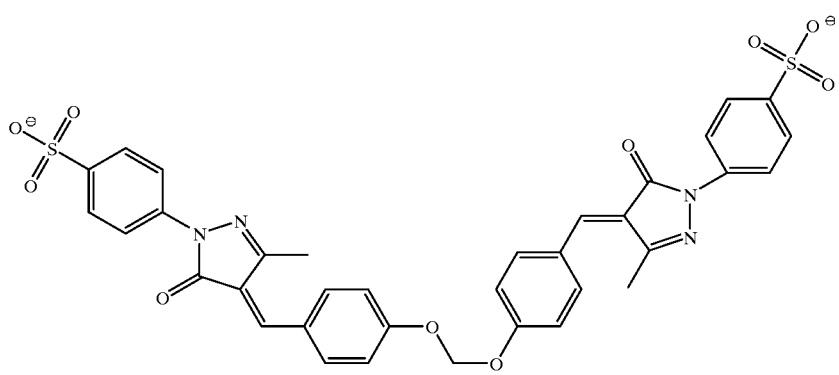
(iv)
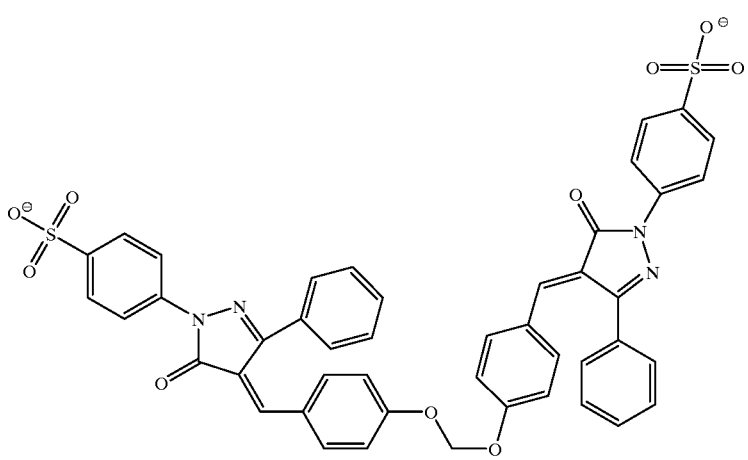
(v)
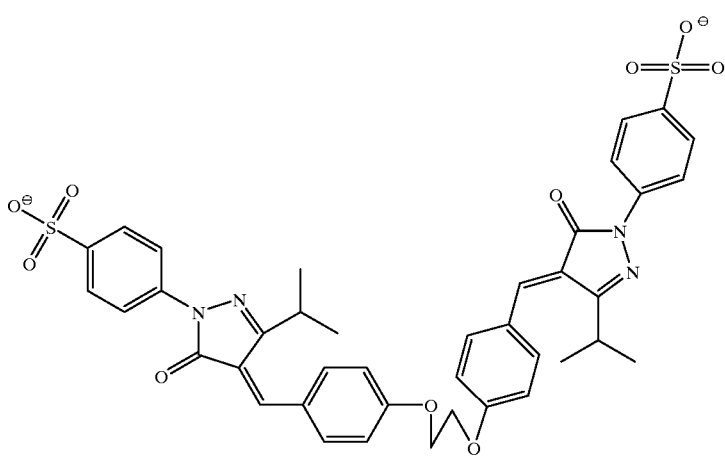
(vi)

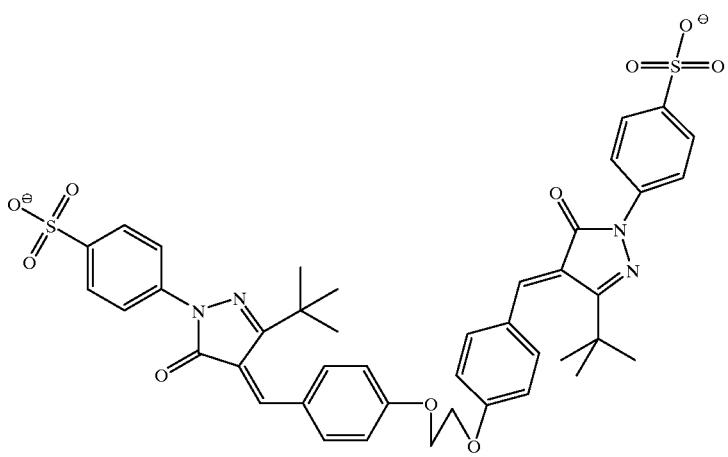
(vii)
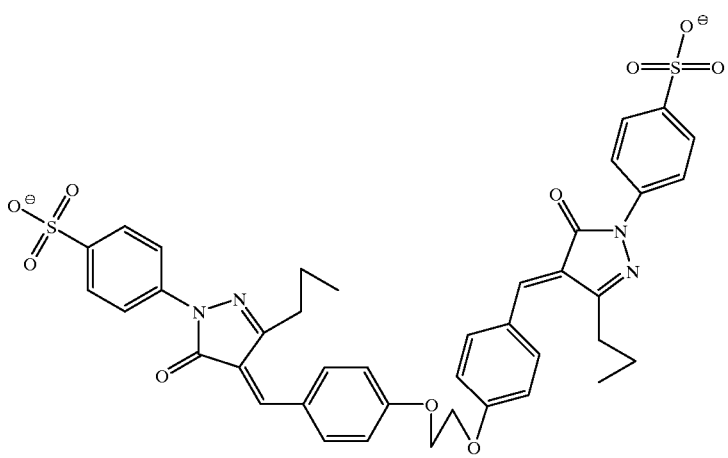
(viii)
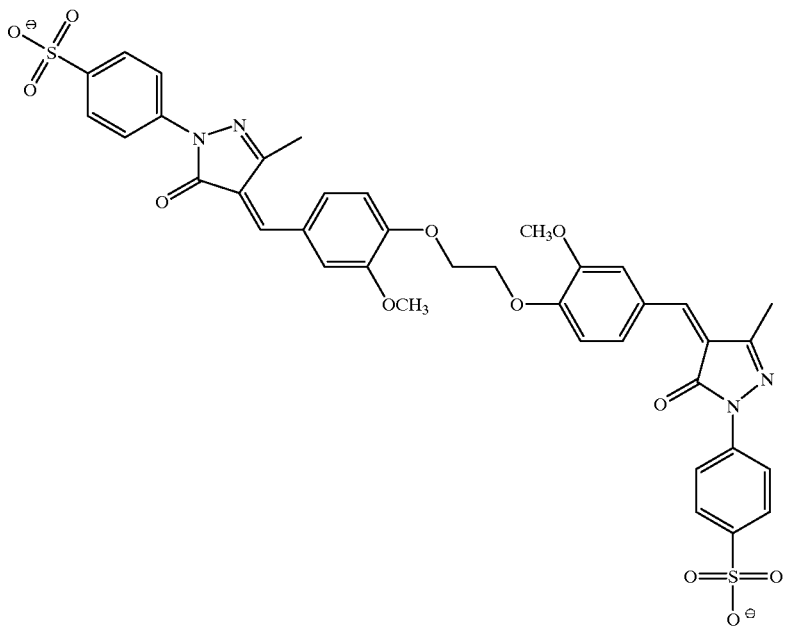
(ix)

-continued
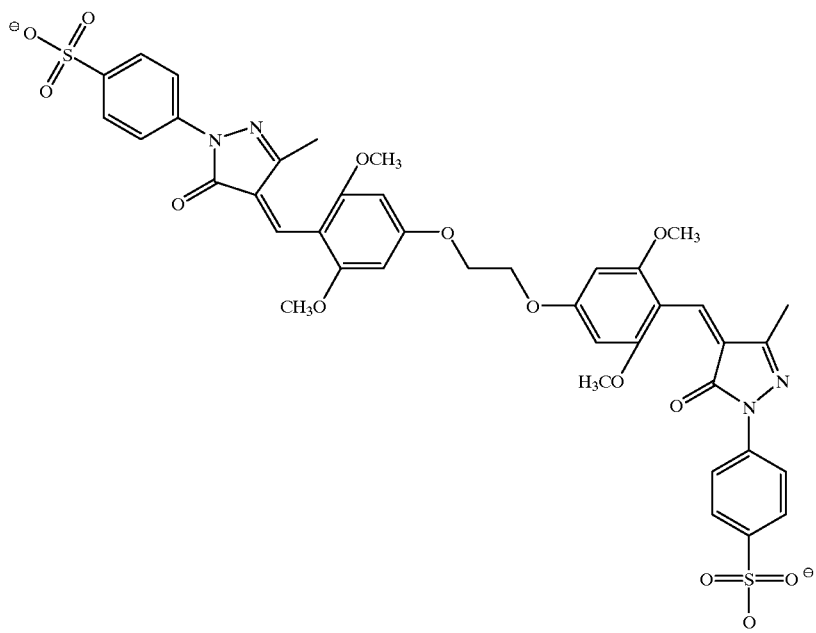
(x)
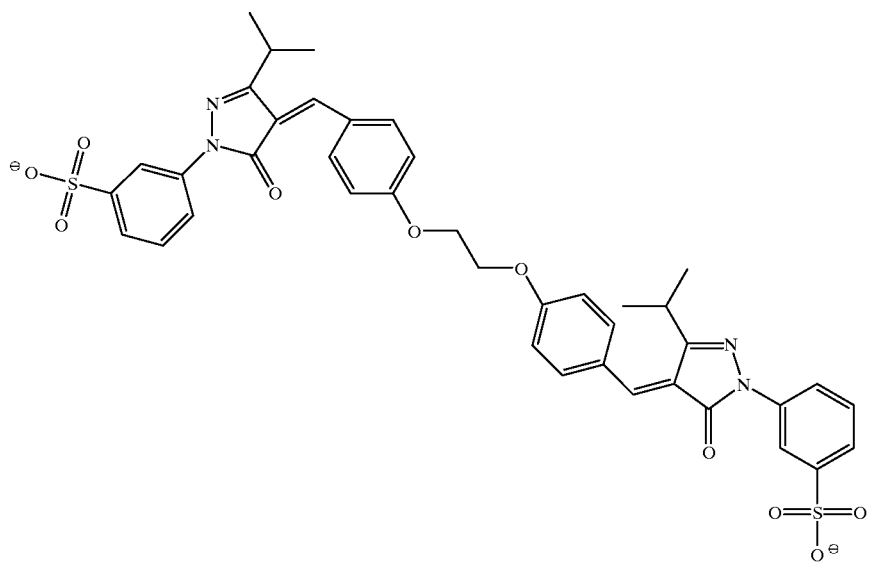
(xi)
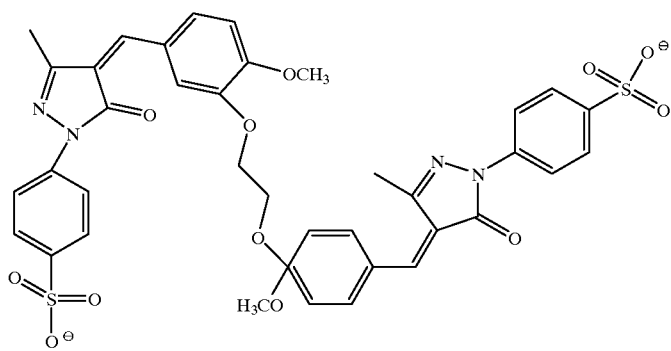
(xii)

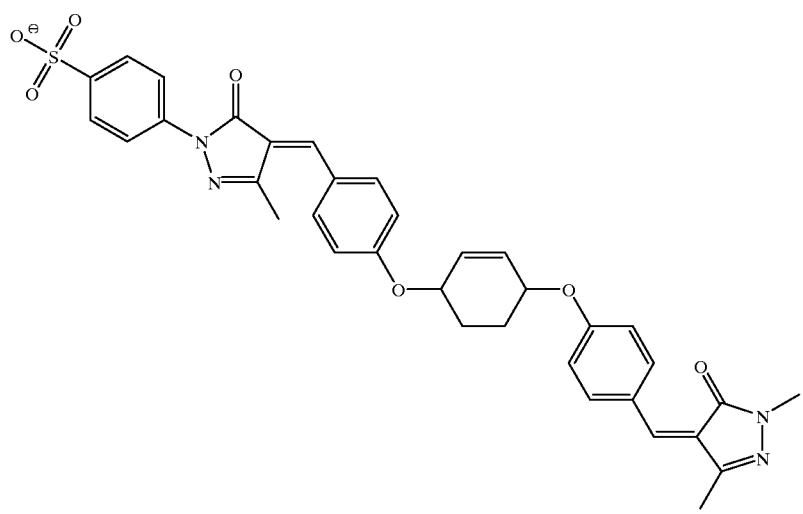
(xiii)